United States Patent [19]

Adams et al.

[11] 4,164,595
[45] Aug. 14, 1979

[54] PREMOISTENED FLUSHABLE WIPER

[75] Inventors: James W. Adams, Schofield; Orville H. Reinke, Oshkosh, both of Wis.

[73] Assignee: American Can Company, Greenwich, Conn.

[21] Appl. No.: 939,288

[22] Filed: Sep. 5, 1978

Related U.S. Application Data

[62] Division of Ser. No. 755,195, Dec. 29, 1976, Pat. No. 4,117,187.

[51] Int. Cl.$^2$ ............................................. B05D 3/10
[52] U.S. Cl. ........................................ 427/341; 162/135; 162/136; 264/128; 427/2; 427/342; 427/377; 427/394; 427/395; 427/411; 427/412
[58] Field of Search ................... 427/2, 411, 412, 342, 427/377, 341, 394, 395; 128/290 R, 290 P, 296; 428/286, 287, 288, 289, 290, 480, 913; 15/104.93, 104.94; 162/136, 135; 264/128

[56] References Cited

U.S. PATENT DOCUMENTS

| | | | |
|---|---|---|---|
| 2,036,036 | 3/1936 | Gibbons | 427/341 |
| 2,170,043 | 8/1939 | Worrall | 427/341 |
| 3,354,032 | 11/1967 | Sommer et al. | 162/136 |
| 3,483,014 | 12/1969 | Isaacs et al. | 427/341 |
| 3,580,253 | 5/1971 | Benardin | 427/341 |
| 3,707,430 | 12/1972 | Costanza et al. | 128/290 |

*Primary Examiner*—Ronald H. Smith
*Assistant Examiner*—J. A. Bell
*Attorney, Agent, or Firm*—Robert P. Auber; Harry C. Engstrom; George P. Ziehmer

[57] ABSTRACT

A premoistened wiper having high initial wet strength in a wetting liquid, and lower wet strength when immersed in substantially neutral water to allow for flushability. The wiper includes a nonwoven web of fibrous material which is bonded together by a polymeric adhesive binder, with the bonded web being moistened until the time of use by a wetting liquid having an acid pH level which is safe for external use on the human body. The binder is composed of a material which is highly adhesive in an acid pH liquid to bind the fibers of the web together, and which is further resistant to weakening over the relatively long periods of shelf life of the wiper. However, the binder loses its binding strength in substantially neutral or alkaline flush water to allow for flushability. The bonded wiper is maintained with wetting liquid thereon within a moisture sealed container until the time of use, and readily loses strength and disintegrates when disposed of in the substantially neutral water of a sewer system.

11 Claims, No Drawings

PREMOISTENED FLUSHABLE WIPER

This is a division of application Ser. No. 755,195, filed Dec. 29, 1976, now U.S. Pat. No. 4,117,187, issued Sept. 8, 1979.

BACKGROUND OF THE INVENTION

1. Field of the Invention

This invention pertains generally to the field of toilet tissue and wipers, and more particularly to premoistened, non-woven wipers.

2. Description of Prior Art

Wipers which are prepackaged in a moist environment are commonly utilized by consumers for cleansing or wiping parts of the body, particularly where wash water is not readily available or cannot be conveniently used. Premoistened wipers are especially convenient for travelers.

The premoistened wiper has found application as an anal cleansing tissue, complimentary to and occasionally a substitute for conventional dry toilet paper. These wipers may also be utilized in applying or removing make-up and in cleansing other parts of the body. Because of such uses, the premoistened wipers are often disposed of by flushing through the toilet systems. Since the premoistened wiper must have sufficient wet strength to resist tearing and puncturing, these wipers do not easily disintegrate in sewer systems and result in plugged drains and sewer laterals.

Typically, the premoistened wipes have consisted of a non-woven web of fibrous material, both natural and synthetic, with the fibers in the web bonded together by an adhesive material having good wet strength qualities. The adhesive binder must also retain strength in the liquid used to wet the web, since this liquid often will contain bactericides and other biological control agents as well as perfumes and emulsifiers to disperse these ingredients. The liquid medium on the web may also be maintained at an acid pH level to further inhibit the growth of organisms. Because the premoistened wiper must necessarily be able to retain its strength in the moist environment in which it is packaged, conventional techniques for achieving disintegration of fabrics in the flush water, such as utilizing ordinary water-soluble fiber binder adhesives, are not practical. Binder adhesives utilized in premoistened wipers must also be capable of maintaining their adhesive strength in a moist environment for a shelf life storage period of from one month to a year or more.

SUMMARY OF THE INVENTION

A premoistened wiper in accordance with this invention is capable of providing high wet strength until used, while disintegrating readily in flush water to allow for flushability and minimal obstruction of sewerage systems. The premoistened wiper has a non-woven web substrate of fibers which are bonded together by a polymeric adhesive, with the bonded web being moistened by a liquid medium having an acid pH level which is safe for external use on the human body. The fibers of the web remain strongly bound together when maintained in the acid pH liquid medium, but are much more loosely bonded when the wiper has been immersed in substantially neutral toilet flush water, allowing the wiper to readily break up in the turbulent movement of the sewerage system.

The non-woven web is preferably formed of relatively short cellulosic fibers, preferably in the range of 1/16 inch to ½ inch, with longer fibers and synthetic fibers being added as desired to provide increased strength in those applications where it is needed. The short cellulosic fibers allow for a relatively soft feel desired in a toilet tissue, while further providing a substrate that is more susceptible to mechanical break-up and disintegration within the sewer system. With such short fibers being utilized, the major strength of the web is provided by the adhesive binder rather than the mechanical entanglement of the fibers of the web. The adhesive binder of the invention is distributed uniformly over the non-woven web, and particularly it has been found that the desired wet strength and flushability may be obtained utilizing binder materials of polymeric adhesives having the property of being weakly adhesive or soluble in a liquid medium of neutral pH or higher, while being strongly adhesive and insoluble in a liquid medium of acid pH. The liquid medium in which the web is maintained is at a low pH to provide the initial wet strength required by the user, while common flush water is of a high enough pH to cause the binder to weaken and allow disintegration of the web. The binder materials of the invention are further resistant to weakening in acid pH solutions such that they may be maintained in moisture sealed packages with the acid pH wetting liquid for relatively long periods of time, as required to obtain the necessary shelf life.

In accordance with the invention, such binder materials in the bonded wiper include acidic polymers, particularly polymeric polycarboxylic acids and polymeric functional derivatives thereof, and copolymers of certain water soluble monomers with water soluble monomers of carboxylic acids or functional derivatives of carboxylic acids. The adhesive binders are further selected from those materials exhibiting a desirable resistance to weakening in acid pH, for the reasons indicated above.

The wetting liquid in which the bonded non-woven web is maintained is acidified by the presence therein of a mineral or organic acid in an amount sufficient to maintain the liquid medium at a desired pH level. The level of pH required in the liquid will vary depending on the type of adhesive binder utilized and the pH level at which it insolubilizes. Generally, to minimize the possibility of skin irritation, the pH of the wetting liquid should be maintained at approximately 2.0 or higher. Other materials may be added to the wetting liquid for various purposes, such as perfumes and bactericides, and the wetting liquid may also contain a soluble surfactant which allows the perfumes and organic growth control agents to be dispersed in the liquid. These surfactants may also be selected to enhance the adhesive properties of the binder.

The binder is produced by forming a web of non-woven materials in a desired conventional fashion, saturating the web either before or after thorough drying with a liquid solution of the binder material in a solvent to cause a pick-up by the web of a desired amount of the binder material, drying of the web to remove the binder solvent, and then immersing the dried web in an acid pH solution which causes the binder material to insolubilize and firmly bind together the fibers of the web. The insolubilizing of the binder adhesive may be accomplished by immersing and maintaining the binder saturated web in the wetting liquid. Alternatively, the binder saturated web may be kept for short periods of time in a relatively low pH solution to thoroughly insolubilize the binder, and after removal of the bonded web from the dipping solution, the wetting liquid is applied to the bonded web and maintained thereon until the time of use. The moistened wipers are packaged in a moisture sealed container, in accordance with conventional packaging techniques, to prevent evaporation of the wetting liquid.

Further objects, features, and advantages will be apparent from the following detailed description illustrating preferred embodiments of the invention.

DESCRIPTION OF THE PREFERRED EMBODIMENTS

A premoistened wiper in accordance with this invention has adequately high wet strength which is maintained over relatively long periods of shelf life, and which is capable of disintegrating when immersed in neutral or basic normal tap water to allow for flushability. Generally, the wipers will be packaged and stacked in a water-tight package, with the wetting liquid applied to the wipers comprising by weight approximately 50% to 300% of the dry weight of the wiper itself. The wiper must maintain its desired characteristics over the time periods involved in warehousing, transportion, retail display, and storage by the consumer. Required shelf lives are in the range of two to six months at a minimum, and the wipers are preferably capable of shelf lives as great as one to two years.

The non-woven web itself is preferably formed of relatively short fibers, such as wood pulp fibers, with the webs being formed by any common web manufacturing process. For example, the web may be produced by a conventional wet laying and wet creping process, or wet laying and through air drying, or by air laying the web, and by other techniques utilized in the paper industry such as those used to produce toweling and tissue paper. Non-woven webs in accordance with this invention are preferably formed to have relatively low wet cohesive strength when they are not bound together by an adhesive. When such fibrous webs are bonded internally by an adhesive which loses its bonding strength in tap water and in sewer water, the webs will thus break up readily in the agitation provided by flushing and moving through the sewer pipes.

The binder of this invention provides for the break-up of the wiper during flushing because of its property of losing bonding strength by dissociation of association complexes between binder and fibers in substantially neutral or basic tap water. Nonetheless, the binder has substantial adhesive strength to hold the web together during the period of shelf life of the wiper and during its use. In accordance with this invention, the binder materials that provide this property are alkali soluble-acid insoluble polymers that provide lasting fiber to fiber bonds in an acid pH wetting liquid. As discussed below, such polymers include polymeric polycarboxylic acids and polymers of functional derivatives thereof, and also polymers of various monomers, particularly vinyl monomers, with monomers of either carboxylic acids or functional derivatives of carboxylic acids.

When polymers containing a large number of ether or ring oxygens, such as cellulose, are mixed with other polymers containing many carboxylic groups, strong association complexes are formed. The points of attachment between the two different kinds of polymer chains are believed to be provided by hydrogen bonds. The association reaction that takes place immediately in water base systems to form strong bonds, can be regulated and reversed by changes in pH. This bonding is believed to be analogous to the association reactions between certain polymers described by K. L. Smith, A. E. Winslow, and D. E. Peterson, "Association Reactions for Poly (alkylene Oxides) and Polymeric Poly (carboxylic Acids)," *Industrial and Engineering Chemistry*, Vol. 51, p. 1361 et seq, November, 1959. The binder molecules bridge between fibers and become attached by hydrogen bonding, thus providing a strong linkage between the fibers of the web. The bonds between the fibers are broken when the bonded wiper is immersed in a liquid medium which has a sufficiently high pH level to break the hydrogen bonds. However, loss of fiber binding strength must be resisted by these binder materials at the low pH levels at which they are maintained until the time of use. The weakening of the bonded wiper in acid pH over a period of time is believed to occur in four ways: (1) depolymerization or cracking of the cellulose fiber molecules in acid solution, (2) scission of the binder molecule polymer chains by hydrolysis to break the binder links between the fibers, (3) leaching of the binder away from the fibers, by hydrolysis or oxidation, which solubilizes the binder, and (4) a material in the wetting liquid other than the binder competes for hydrogen bonding sites on the fibers and displaces the binder therefrom. The first cause of weakening of the bonded web is largely independent of the binder chosen since the breakdowns occur in the cellulose fibers. The other causes of weakening are more or less dependent on the binder material.

Generally good adhesive properties which satisfy the requirements above are obtained with acidic polymers having equivalent weights between 100 and 500 and molecular weights between approximately 20,000 and 1,000,000. Polymers of various carboxylic acids alone which meet these criteria will provide the qualities required for an effective binder. Particularly good results are also obtained with binders formed of copolymers of water soluble or insoluble monomers with water soluble monomers which are either carboxylic acids or functional derivatives thereof. By way of illustration but not limitation, such copolymers include the following: styrene and maleic anhydride; methyl methacrylate and acrylic acid; ethyl acrylate and acrylic acid; vinyl acetate and crotonic acid; acrylate esters and acrylic acid; methacrylate esters and acrylic acid; acrylate esters and methacrylic acid; and methacrylate esters and methacrylic acid. It has been found, however, that not all such carboxylic acid polymers and their derivatives have the necessary resistance to weakening over reasonable shelf life periods. For example, commercially available sodium carboxy methylcellulose provides good initial wet strength when deposited on the fibers of a web and acidified, but rapidly weakens through hydrolysis, primarily by chain scission, when maintained in an acid medium, and this material loses most of its binding strength within a month.

The binder material is prepared for application to a web by dissolving in water using enough alkali to substantially neutralize all acidic groups. The polymer solution, comprising a water solution of a salt of the acidic polymer, can then be applied to the web by various processes, including dipping the web in the polymer solution to cause complete saturation of the web with the solution, or spraying or rolling the solution onto the web such that the polymer solution thoroughly saturates through the web to contact the fibers therein and fill in the spaces in the web between the fibers. The saturated web is then dried to substantially remove the solvent water and allow the binder material molecules to settle into positions in which they can form linkages between the fibers. After drying, the binder saturated web is then immersed in a liquid medium which has a low pH to cause association reactions to take place between binder and fiber. The acid pH may be provided in the solution by any suitable acid including hydrochloric, oxalic, fumaric, malic and phosphoric acid, or other mineral or organic acids which will not react with the binder material and which will not present safety problems when the wiper is used on the human body. Similarly, the wetting liquid in which the bonded web is maintained until the time of use will include an acid, such as those listed above, to control the pH of the wetting liquid at a level at which the bonding in the adhesive binder remains strong. Other ingredients will also be present in the wetting liquid, such as perfumes, bactericides, ethyl alcohol, and emulsifiers and surfactants to allow dispersion of the other ingredients within the wetting liquid.

It is found that the surfactants utilized in the wetting liquid can have a substantial effect on the quality of the binding of the web. For example, nonionic emulsifiers in the wetting liquid tend to weaken the binder. It is theorized that the emulsifiers compete for hydrogen bonding sites with the molecules of the binder and thus weaken the quality of the bonds. Conversely, the use of anionic surfactants, particularly those having a carboxylic base, do not substantially weaken the binder, and actually increase the wet strength above the level found without the use of such surfactants. For example, the bonding may be strengthened by the use of sulfonic dispersants (e.g. polymerized sodium salts of alkyl naphthalene sulfonic acid) and carboxy dispersants (sodium salts of polycarboxylic acid and polyacrylic acid). These dispersants also do not substantially affect the loss of strength that occurs when the wiper is immersed in neutral water solution, and do not substantially inhibit the solubility of the binder itself.

The following examples are provided as illustrative of the invention, but are not to be construed as being exhaustive or as limiting the invention to the specific details thereof.

EXAMPLES 1-4

In the examples that follow, the measurement of wet and dry tensile strength was determined according to the following method. Six inch by six inch sheets of the selected non-woven web were heated in an oven at 105° C. for 15 minutes. The dry sheets were then stored in a desiccator loaded with Drierite calcium sulfate. Two dry 6×6 inch sheets were weighed separately, and were then saturated in the binder solution under test and passed through rubber ringer rolls to remove excess liquid. The sheets were placed side-by-side between two pieces of 20 mesh Teflon screen and dried in a photographic print dryer set at 105° C. for 5 minutes, and were then cooled in a desiccator. The resulting substantially dry sheets contained less than 10% water on the dry weight of the web. Overdrying of the webs to moisture levels below 1 or 2% at elevated temperatures is avoided because heating for prolonged periods of time will cross-link the binder material. The dried sheets were weighed, and four 1×4 inch strips from each sheet were cut. Where the web was a creped web, the sheets were cut such that the creping wrinkles ran with the long 4 inch dimension of the strip to allow measurement of the tensile strength of the web in the cross machine direction (CD) of the web. The dry weight binder content of the web, in grams of binder per 100 grams of dry weight web, was calculated by subtracting the initial dry weight of the web from the weight of the web after applying the binder and drying, dividing that quantity by the initial weight of the web and multiplying by 100 grams. 100 ml. of 500 mg./liter phosphoric acid solution was placed in a clean square petri dish. The eight strips of paper were immersed in the acid liquid and allowed to soak at room temperature for eighteen hours. The pH of the soaking liquid was measured at the beginning and end of the soaking time. After soaking, the strips were blotted between two paper towels and the tensile strength of four wet, acid soaked strips were measured. The other four strips were placed in two liters of tap water contained in a four liter beaker. An electric mixer equipped with a 2 inch marine impeller was positioned near the center of the four liter beaker such that the bottom of the impeller was one inch from the surface of the water. The impeller was turned on at a speed of 100 rpm for one hour. The strips were then removed, blotted between paper towels and the wet tensile strengths measured.

To determine relative break-up times between different treated wipers, the following testing procedure was utilized. A Tergotometer (Model 7243, United States Testing Co., Inc., 1415 Park Ave., Hobokken, N.J.) was modified such that each two liter stainless steel beaker in the Tergotometer will allow overflow of water into the temperature control chamber. Nineteen 3/16 inch diameter holes were drilled in each tub, spaced equally in a ring around the wall of the tub, at a distance four inches from the bottom of the tubs. Each tub was equipped with a separate cold water supply line and a flow meter capable of measuring flows of 500 to 1,000 ml./min. 3×3 inch squares of the wiper to be tested were cut, and all three squares were put in one 2-liter stainless steel tub in the Tergotometer. The tub was filled with cold tab water and the agitator started running at 100 cycles per minute. Cold tap water was run into the mixing system at a flow rate of 800 millimeters per minute. Liquid is allowed to overflow through the perforations in the tub. The time was measured from the start of mixing, and mixing was continued until all three squares of wiper were broken down to pieces smaller than ¾ inch in diameter. The elapsed time required to obtain the specified degree of break-up was recorded for each test.

The following binder solutions were prepared:

Two percent acrylic acid-acrylic ester copolymer solution was prepared by mixing 46 grams of 40% solids Acrysol ASE-75 Latex obtained from the Rohm & Haas Co., with 926 grams of distilled water. Twenty-eight grams of 10% sodium hydroxide was added thereto to neutralize the solution.

Two percent acrylic acid-acrylic ester copolymer solution was prepared by mixing 70 grams of 25% solids XD-30070 Latex from Dow Chemical Company, with 900 grams of distilled water. Thirty grams of 10% sodium hydroxide was added thereto to neutralize the solution.

Two percent styrene-maleic anhydride copolymer solution was prepared by dissolving 20 grams of Scriptset 500 powder obtained from the Monsanto Company, in 980 grams of distilled water. The mixture was heated and stirred as necessary to result in complete solution of the powder.

A two percent vinyl acetate-crotonic acid copolymer solution was prepared from a concentrate formed by stirring 120 grams of Vinac ASB-516 obtained from Air Products & Chemicals Company, and 1,025 grams of distilled water containing 55 grams of 10% sodium hydroxide. Two hundred grams of the concentrate was mixed with 800 grams of water and was heated and stirred to completely dissolve the polymer. A five percent vinyl acetate-crotonic acid copolymer was also prepared for subsequent procedures by mixing 500 grams of the concentrate with 500 grams of water, and was heated and stirred to completely dissolve the polymer.

A standard, non-woven substrate web for evaluating the binders was made by refining a mixture of 75% bleached softwood kraft (SWK) pulp and 25% bleached hardwood kraft (HWK) pulp fibers to a Canadian standard freeness of 550 ml. The refined pulp was processed on a commercial paper machine to make wet creped paper with a basis weight of 40 lbs./3,000 sq. ft.

The procedures specified above for determining wet tensile strength and break-up time were utilized for each of the two percent concentration binder solutions to obtain the data set forth in Table I below. The amount of binder pickup by the web in terms of the dry weight of the binder material to the dry weight of the web is also given in Table I.

TABLE I

| Binder | Polymer Type | Binder in Web g./100 g. | CD Wet Tensile q./cm. Dilute Acid | CD Wet Tensile q./cm. Tap Water | Breakup Time, Min. |
| --- | --- | --- | --- | --- | --- |
| 12% Acrysol ASE-75 | Acrylic acid-acrylic ester copolymer | 2.5 | 340 | 160 | 30 |
| 2% Dow XD-30070 | Acrylic acid-acrylic ester copolymer | 3.1 | 395 | 98 | 18 |
| 2% Scripset 500 | Styrene-maleic anhydride copolymer | 3.6 | 190 | 114 | 25 |
| 2% Vinac ASB-516 | Vinyl acetate-crotonic acid copolymer | 2.2 | 123 | 87 | 4 |

EXAMPLES 5-8

Fibers composed of 75% bleached Canadian softwood kraft pulp and 25% 1.5 denier rayon fibers, cut to ¼ inch length, were slurried in water and made into a paper web having a basis weight of 30 lbs./3,000 sq. ft. on handsheet equipment. The dried sheets were dipped in the four two percent binder solutions specified above in Examples 1-4 and dried, and the procedures outlined in Examples 1-4 were followed to determine wet tensile strength and breakup time. The results of these tests are given below in Table II.

TABLE II

| Binder | Polymer Type | Binder in Web g./100 g. | CD Wet Tensile g./cm. Dilute Acid | CD Wet Tensile g./cm. Tap Water | Breakup Time, Min. |
| --- | --- | --- | --- | --- | --- |
| 2% Acrysol ASE-75 | Acrylic acid-acrylic ester copolymer | 2.3 | 126 | 67 | 6 |
| 2% Dow XD-30070 | Acrylic acid-acrylic ester copolymer | 5.2 | 102 | 29 | 5 |
| 2% Scripset 500 | Styrene-maleic anhydride copolymer | 3.4 | 88 | 55 | 2 |
| 2% Vinac ASB-516 | Vinyl acetate-crotonic acid copolymer | 2.3 | 87 | 56 | 3 |

EXAMPLES 9-22

Forty lbs./3,000 sq. ft. wet creped paper, made from 75% softwood kraft and 25% hardwood kraft pulp, was dipped in and saturated with 2% sodium Acrysol ASE-75 (acrylic acid-acrylic ester copolymer) water solution and dried. Samples of this paper were separately soaked in acidifying solutions containing four different acids at various levels of concentration, as indicated below.

Four acid stock solutions were prepared to yield acid reagent concentrations of 0.01 grams/ml. of water, as follows:

| Acid | Type | Acid Amount, g. | Distilled Water Amount, g. |
| --- | --- | --- | --- |
| Hydrochloric 37% HCl | Strong Mineral | 27 | 973 |
| Phosphoric 85% $H_3PO_4$ | Weak Mineral | 11.8 | 988 |
| Oxalic Oxalic Acid · $2H_2O$ | Strong Organic | 14 | 986 |
| Malic 100% | Weak Organic | 10 | 990 |

-continued

| Acid | Type | Acid Amount, g. | Distilled Water Amount, g. |
|---|---|---|---|
| Malic Acid | | | |

The tensile strengths of the bonded web samples after soaking in the acid solutions for eighteen hours, were measured in accordance with test procedures specified in the foregoing Examples. Acid pH values were recorded in the soaking solutions before and after the bonded web was soaked. The tensile strength of the web after soaking is given below in Table III. The wet tensile strength for a web sample soaked in water alone is also given in Table III for comparison purposes.

TABLE III

| Acid | Stock Diluted to 1 liter (ml. of stock) | Concentration mg./liter | Solution pH Initial | Solution pH After Soaking Web | CD Wet Tensile g./cm. |
|---|---|---|---|---|---|
| None | — | — | 6.7 | 7.4 | 64 |
| HCl | 5 | 50 | 2.8 | 3.3 | 170 |
| " | 10 | 100 | 2.5 | 2.8 | 238 |
| " | 15 | 150 | 2.3 | 2.6 | 308 |
| " | 20 | 200 | 2.2 | 2.4 | 333 |
| $H_3PO_4$ | 10 | 100 | 2.9 | 3.6 | 205 |
| " | 20 | 200 | 2.7 | 3.0 | 248 |
| " | 40 | 400 | 2.4 | 2.7 | 310 |
| " | 60 | 600 | 2.3 | 2.5 | 345 |
| Oxalic | 10 | 100 | 2.8 | 3.3 | 205 |
| " | 20 | 200 | 2.5 | 2.8 | 266 |
| " | 50 | 500 | 2.2 | 2.4 | 370 |
| Malic | 20 | 200 | 3.1 | 3.7 | 217 |
| " | 40 | 400 | 3.0 | 3.3 | 278 |
| " | 80 | 800 | 2.8 | 3.0 | 315 |

EXAMPLES 23–46

A 2% Acrysol ASE-75 solution and 2% and 5% Vinac ASB-516 solutions were prepared as outlined in Examples 1–4 for use as binders for a variety of nonwoven web substrates. Conventional wet laid, paper was prepared from the following fibers:

(1) Bleached Canadian softwood kraft (SWK) pulp.
(2) Bleached Canadian hardwood kraft (HWK) pulp.
(3) 1.5 denier rayon chopped to ¼-inch length.
(4) A blend of 75% SWK and 25% chopped ¼-inch length rayon.
(5) A blend of 75% SWK and 25% 3.0 denier Kuralon No. 4, polyvinylalcohol fibers, chopped to ¼-inch length.
(6) Cotton linters.
(7) A blend of 75% SWK and 25% cotton linters.
(8) 1.5 denier polyester fibers chopped to 9/16 inch length.

The test procedures specified above in Examples 1–4 were used to saturate all of the webs with the various binders and to acidify the webs in phosphoric acid solution to insolubilize the binder. The procedures of Examples 1–4 were also utilized to determine wet tensile strength after soaking in acid and after soaking in substantially neutral tap water, and to determine the breakup time after soaking in the tap water. This data is given in Table IV below.

TABLE IV

| Substrate | Fiber Binder | CD Wet Tensile,g/cm Dil. Acid | CD Wet Tensile,g/cm Tap Water | Breakup Time, Min. |
|---|---|---|---|---|
| Bl. SW kraft paper | 2% Acrysol | 200 | 82 | 8 |
| | 2% Vinac | 98 | 54 | 2 |
| | 5% Vinac | 165 | 75 | 9 |
| Bl. HW Kraft paper | 2% Acrysol | 92 | 36 | 8 |
| | 2% Vinac | 65 | 26 | 2 |
| | 5% Vinac | 100 | 48 | 6 |
| 1/4-inch rayon | 2% Acrysol | 46 | 22 | 0.5 |
| | 2% Vinac | 28 | 9 | 1 |
| | 5% Vinac | 42 | 40 | 2 |
| 75% SW kraft and 25% Rayon | 2% Acrysol | 137 | 76 | 7 |
| | 2% Vinac | 98 | 53 | 2 |
| | 5% Vinac | 170 | 92 | 7 |
| 75% SW kraft and 25% Kuralon | 2% Acrysol | 170 | 68 | 10 |
| | 2% Vinac | 91 | 36 | 2 |
| | 5% Vinac | 160 | 80 | 8 |
| Cotton linters | 2% Acrysol | 16 | 14 | 10 |
| | 2% Vinac | 31 | 17 | 10 |
| | 5% Vinac | 67 | 35 | 10 |
| 75% SW kraft and 25% cotton | 2% Acrysol | 39 | 27 | 3 |
| | 2% Vinac | 33 | 14 | 1 |
| | 5% Vinac | 68 | 35 | 4 |
| 9/16-inch polyester | 2% Acrysol | 121 | 93 | 1 |
| | 2% Vinac | 390 | 210 | 6 |
| | 5% Vinac | 1150 | 830 | 12 |

Generally, premoistened wipers in practical application must be strong enough so that they will not tear when pulled from dispensing containers, or puncture when used for wiping. It has been found that wet wipers with tensile strengths of 140 g./cm. or higher satisfactorily meet this requirement. To obtain desirable breakup of the wipers in toilet flush water, it is preferred that the tensile strength of the wiper immersed in neutral water should drop below approximately 70 g./cm. It may be noted, however, that lower wet strengths are satisfactory where the dispensing of the wipers from their packaging does not require vigorous pulling and strain on the wipers. Furthermore, the decrease in tensile strength and breakup time after neutral water soak which is associated with all of the binders of this invention is of substantial utility in preventing clogged drains and sewer systems, even where the strengths of the wiper in neutral flush water are not as low as are obtained with standard dry tissue paper.

EXAMPLES 47–50

A 40 lb./3,000 sq. ft. web of wet creped paper made from 75% softwood kraft and 25% hardwood kraft fibers was saturated with bonding solutions at four concentration levels. Four Acrysol ASE-75 (acrylic acid-acrylic ester copolymer) solutions were prepared at concentration levels of 1%, 2%, 3%, and 4% as indicated below:

|  | 1% | 2% | 3% | 4% |
|---|---|---|---|---|
| Water, grams | 963 | 926 | 889 | 852 |
| 40% Acrysol ASE-75 Latex, g. | 23 | 46 | 69 | 92 |
| 10% NaOH, g. | 14 | 28 | 42 | 56 |

The wet strength of the wiper after acid soak, and the wet strength and breakup time after water soak were determined according to the procedures specified in Examples 1–4 above. The resulting data are given in Table V below. Test results for a web having no binder are also given in Table V for comparison purposes.

TABLE V

| Na Acrysol ASE-75 in Dip, % | Acrysol Pickup, g./100 g. fiber | CD Wet Tensile, grams/cm. | | Breakup Time, minutes |
| | | Dilute Acid | Tap Water | |
|---|---|---|---|---|
| None | — | 55 | — | 1 |
| 1 | 1.1 | 220 | 107 | 12 |
| 2 | 3.1 | 328 | 144 | 38 |
| 3 | 5.2 | 278 | 185 | 45 |
| 4 | 7.9 | 257 | 154 | 54 |

EXAMPLES 51–54

A web substrate formed of Canadian softwood kraft pulp was soaked in a water solution of 75% neutralized Sodium Acrysol ASE-75 binder, with a resulting pickup of 2.7 grams of binder per 100 grams of dry web. The bonded web was immersed in water solutions of four acids, phosphoric, hydrochloric, oxalic, and malic. The cross machine dimension (CD) wet tensile strength of the bonded webs was measured after initial 18 hour soaking in the acid solutions and again after six months of soaking in the acid solutions. These data are given below in Table VI, which also gives the pH of the acid solution at the beginning and at the end of the six month period.

TABLE VI

| Binder | | | pH | | CD Wet Tensile, grams/cm. | |
| Type | Pickup, g./100 g. | Acid | Start | 6 Months | Start | Months |
|---|---|---|---|---|---|---|
| Acrysol ASE-75 (75%) Neut.) | 2.7 | H$_3$PO$_4$ | 2.50 | 2.55 | 329 | 215 |
| | | HCl | 2.60 | 2.60 | 244 | 179 |
| | | Oxalic | 2.51 | 5.10 | 289 | 217 |
| | | Malic | 2.51 | 2.71 | 461 | 419 |

It is apparent that the bonded web loses some tensile strength over the aging period, with this weakening being due to the mechanisms discussed above, including breakdown of the cellulosic fibers in the web. These binders are, however, substantially resistant to weaking such as by chain scission, since the tensile strengths of the aged bonded webs are far greater than the tensile strength of an unbonded web, which is generally about 50 to 60 g./cm. or less.

EXAMPLES 55–57

A mixture of 75 parts bleached softwood kraft pulp and 25 parts bleached hardwood kraft pulp was refined to a Canadian standard freeness of 550 ml., and was processed on a commercial paper machine to make a wet creped paper with a basis weight of 40 lbs./3,000 sq. ft. The dry paper was saturated with a solution of 2% sodium Acrysol solution (sodium acrylic acid-acrylic ester copolymer) made by mixing 46 grams of 40% solids Acrysol ASE-75 obtained from the Pohm & Haas Co., with 926 grams of distilled water. The Acrysol was neutralized by adding 28 grams of 10% sodium hydroxide. The dried saturated web contained 2.4 grams sodium Acrysol per 100 grams of the web itself. A first wetting liquid was prepared comprising 993 grams of distilled water, 4 grams of 85% phosphoric acid, and 3 grams of Daxad 11 from W. R. Grace Co., a sulfonic dispersant (polymerized sodium salts of alkyl naphtalene sulfonic acid). A second wetting liquid was prepared comprising 986 grams of distilled water, 4 grams of 85% phosphoric acid, and 10 grams of Tamol 850 from the Rohm & Haas Co., a carboxy dispersant. A third wetting liquid was prepared comprising 991 grams distilled water, 4 grams 85% phosphoric acid, and 4.6 grams Goodrite K743 from B. F. Goodrich Co., a polyacrylic acid. Sheets of the binder saturated dried paper were moistened with the three wetting liquids, squeezed to remove excess liquid, and stored wet for 24 hours. Cross machine direction (CD) tensile strength measurements before and after soaking in tap water were determined as indicated in Examples 1-4 above. These data are given in Table VII, along with similar data for a bonded sheet stored in an acid wetting liquid which contained no dispersant.

TABLE VII

| Surfactant | pH of Acid Soak | CD Wet Tensile, g./cm. | | Breakup Time Minutes |
|---|---|---|---|---|
| | | Initial | After 1-Hour Water Soak | |
| None | 2.4 | 449 | 248 | 30 |
| Sulfonic Dispersant (Daxad 11) | 2.0 | 489 | 237 | 40 |
| Carboxy Dispersant (Tamol 850) | 2.8 | 457 | 176 | 34 |
| Polyacrylic acid (Goodrite K743) | 1.9 | 511 | 193 | 44 |

These dispersants thus allow incorporation of the desired non-water soluble ingredients into the wetting liquid, while maintaining or enhancing the wet strength of the bonded web, and do not substantially affect the loss of strength of the bonded web when immersed in neutral water. Ethyl alcohol may also be added to the wetting liquid to aid in emulsification of the perfumes and organic stabilizers.

The wetting liquid is maintained on the bonded wiper and evaporation prevented by sealing the wetted wipers in a moisture proof container. The acidity of the wetting liquid aids in maintaining the organic stability of the packaged wipers, since low pH inhibits the growth of some organisms, particularly where the pH is maintained below about 4.0 or 5.0. Since very low pH levels can result in irritation of human skin, it is preferred that the pH of the wetting liquid be greater than approximately 2.0. This level of acidity is not unusual in consumer products. For example, most soft drinks have a pH level between about 2.0 and 4.0.

It is understood that the invention is not confined to the particular embodiments described herein as illustrative of the invention, but embraces all such modifications thereof as may come within the scope of the following claims.

We claim:

1. A process for producing a premoistened wiper having high initial wet strength and lower wet strength when immersed in a substantially neutral or alkaline liquid to allow for flushability, comprising the steps of:
   (a) forming a non-woven web of fibrous materials;
   (b) forming a liquid binder solution consisting essentially of water and a salt of an acid insoluble-alkali soluble acidic polymer which is capable of bonding together the fibers of said web in acid liquid and is resistant in acid liquid to weakening of the bonding between the fibers;
   (c) applying said liquid binder solution in a uniform distribution through said web;
   (d) drying said web to substantially remove the water therefrom; and
   (e) immersing said dried web in an acid liquid to bond together the fibrous material to said web with said acidic polymer.

2. The process of claim 1 including the additional steps of applying an acid wetting liquid to said bonded web, and enclosing said web and wetting liquid in a moisture sealed container.

3. The process of claim 2 wherein said wetting liquid consists essentially of a solution of water and an acidifying agent selected from the group consisting of phosphoric acid, malic acid, fumaric acid, oxalic acid, and hydrochloric acid, said acidifying agent being present in said wetting liquid in an amount sufficient to maintain said wetting liquid on said bonded web at a pH of no greater than 5.0.

4. The process of claim 2 wherein said wetting liquid includes therein a surfactant selected from the group consisting of sulfonic surfactants and carboxy surfactants.

5. The process of claim 2 wherein said wetting liquid includes therein a surfactant selected from the group consisting of polymerized sodium salts of alkyl naphthalene sulfonic acid, sodium salts of carboxylic acids, and polyacrylic acid.

6. The process of claim 1 wherein said acidic polymer is an acid insoluble-alkali soluble polymeric polycarboxylic acid which is resistant in acid liquid to weakening of the bonding between the fibers of said web.

7. The process of claim 1 wherein said acidic polymer is an acid insoluble-alkali soluble polymeric functional derivative of a polycarboxylic acid which is resistant in acid liquid to weakening of the bonding between the fibers of said web.

8. The process of claim 1 wherein said acidic polymer is an acid insoluble-alkali soluble polymer of a monomer material with a carboxylic acid and which is resistant in acid liquid to weakening of the bonding between the fibers of said web.

9. The process of claim 1 wherein said acidic polymer is an acid insoluble-alkali soluble polymer of a monomer material and a functional derivative of a carboxylic acid and which is resistant in acid liquid to weakening of the bonding between the fibers of said web.

10. The process of claim 1 wherein said acidic polymer is selected from the group consisting of a copolymer of styrene and maleic anhydride, a copolymer of acrylate esters and methacrylic acid, a copolymer of methyl methacrylate and acrylic acid, a copolymer of acrylate esters and acrylic acid, a copolymer of methacrylate esters and acrylic acid, a copolymer of ethyl acrylate and acrylic acid, a copolymer of vinyl acetate and crotonic acid, and a copolymer of methacrylate esters and methacrylic acid.

11. The process of claim 1 wherein the fibrous material of said non-woven web is selected from the group consisting of fibers of wood pulp, rayon, cotton, polyvinylalcohol, polyester and mixtures thereof.

* * * * *